United States Patent
Ferguson et al.

(10) Patent No.: US 9,261,438 B2
(45) Date of Patent: Feb. 16, 2016

(54) MATRIX ASSISTED LASER DESORPTION IONISATION MASS SPECTROMETRY IMAGING (MALDI-MSI)

(75) Inventors: Leesa Susanne Ferguson, Sheffield South Yorkshire (GB); Rosalind Wolstenholme, Sheffield South Yorkshire (GB); Simona Francese, Sheffield South Yorkshire (GB)

(73) Assignee: SHEFFIELD HALLAM UNIVERSITY, Sheffield South Yorkshire (GB)

( * ) Notice: Subject to any disclaimer, the term of this patent is extended or adjusted under 35 U.S.C. 154(b) by 0 days.

(21) Appl. No.: 14/003,813

(22) PCT Filed: Mar. 1, 2012

(86) PCT No.: PCT/GB2012/050460
§ 371 (c)(1),
(2), (4) Date: Dec. 3, 2013

(87) PCT Pub. No.: WO2012/120279
PCT Pub. Date: Sep. 13, 2012

(65) Prior Publication Data
US 2014/0084151 A1    Mar. 27, 2014

(30) Foreign Application Priority Data

Mar. 9, 2011   (GB) .................................. 1104003.7
Mar. 15, 2011  (GB) .................................. 1104365.0

(51) Int. Cl.
*H01J 49/00* (2006.01)
*G01N 1/28* (2006.01)
(Continued)

(52) U.S. Cl.
CPC ............... *G01N 1/28* (2013.01); *A61B 5/1172* (2013.01); *G01N 1/2813* (2013.01); *G06K 9/00013* (2013.01); *H01J 49/0004* (2013.01);
(Continued)

(58) Field of Classification Search
USPC ......................................................... 250/282
See application file for complete search history.

(56) References Cited

U.S. PATENT DOCUMENTS 3,075,852 A    1/1963  Bonora
4,143,544 A *  3/1979  DeVries et al. ................. 73/104
(Continued)

FOREIGN PATENT DOCUMENTS

WO    WO 2010/007443 A2    1/2010

OTHER PUBLICATIONS

Rowell; et.al., "Detection of drugs and their metabolites in dusted latent fingermarks by mass spectrometry", Analyst, 2009,134, 701-707.*

(Continued)

*Primary Examiner* — Phillip A Johnston
(74) *Attorney, Agent, or Firm* — Kirton McConkie; Evan R. Witt

(57) ABSTRACT

A method of preparing a sample for matrix assisted laser desorption ionization mass spectrometry imaging analysis by a two-step process. Firstly, a MALDI matrix is dusted on to the sample followed by a spray of a suitable solvent onto the dusted sample. The present method has been successfully applied to the detection and mapping of several analyte classes in latent fingermarks. Using the present two-step method, fingermark enhancement, recovery and analysis from different substrate surfaces is now possible enabling visual and chemical information to be obtained simultaneously via remote testing.

20 Claims, 12 Drawing Sheets

(51) Int. Cl.
*A61B 5/117* (2006.01)
*H01J 49/16* (2006.01)
*G06K 9/00* (2006.01)
*H01J 49/04* (2006.01)
*G01N 1/00* (2006.01)
*G01N 1/02* (2006.01)

(52) U.S. Cl.
CPC .......... *H01J49/0418* (2013.01); *H01J 49/164* (2013.01); *G01N 2001/007* (2013.01); *G01N 2001/028* (2013.01)

(56) References Cited

U.S. PATENT DOCUMENTS

| | | | |
|---|---|---|---|
| 4,708,882 A | 11/1987 | Asano et al. | |
| 5,099,131 A | 3/1992 | Brownrigg et al. | |
| 5,594,243 A * | 1/1997 | Weinberger | H01J 49/025 250/281 |
| 5,700,272 A * | 12/1997 | Gordon et al. | 606/144 |
| 6,900,061 B2 * | 5/2005 | Smirnov | B01L 3/5085 250/288 |
| 7,923,682 B2 * | 4/2011 | Rowell | C09C 1/3081 250/287 |
| 8,778,695 B2 * | 7/2014 | Caprioli | G01N 33/6848 436/173 |

OTHER PUBLICATIONS

Agar, Nathalle Y.R. et al., "Matrix Solution Fixation: Histology-Compatible Tissue Preparation for MALDI Mass Spectrometry Imaging", Anal. Chem. 2007, 79, pp. 7416-7423.
Ricci, Camilla et al., "Spectroscopic Imaging of Latent Fingermarks Collected with the Aid of a Gelatin Tape", Anal. Chem. 2007, 79, pp. 5771-5776.
Wolstenhome, Rosalind et al., "Study of Latent Fingermarks by Matrix-Assisted Laser Desorption/Ionisation Mass Spectrometry Imaging of Endogenous Lipids", Rapid Communications in Mass Spectrometry, Rapid Commun. Mass Spectrom. 2009; 23: pp. 3031-3039.
Sugiura, Yuki et al., "Two-Step Matrix Application Technique to Improve Ionization Efficiency for Matrix-Assisted Laser Desorption/Ionization in Imaging Mass Spectrometry", Anal. Chem. 2006, 78, pp. 8227-8235.
Goodwin, R.J.A. et al., "Use of a Solvent-Free Dry Matrix Coating for Quantitative Matrix-Assisted Laser Desorption Ionization Imaging of 4-Bromophenyl-1,4-Diazabicyclo(3.2.2)Nonane-4-Carboxylate in Rat Brain and Quantitative Analysis of the Drug from Laser Microdissected Tissue Regions", American Chemical Society, Analytical Chemistry, 2010, pp. A-F.
Crossman, Lee et al., "Investigation of the Profiling Depth in Matrix-Assisted Laser Desorption/Ionization Imaging Mass Spectrometry", Rapid Communications in Mass Spectrometry, Rapid Comm. Mass Spectrom. 2006; 20: pp. 284-290.
Belgorodsky, Bogdan et al., "First Year Annual Report—Grant #093084", School of Chemistry, Tel Aviv University, Israel, Apr. 23, 2010, Report Documentation Page and pp. 1-9.
Ferrer, Imma et al., "Identificatiion of Alkyl Dimethylbenzylammonium Surfactants in Water Samples by Solid-Phase Extraction Followed by Ion Trap LC/MS and LC/MS/MS", Environ. Sci. Technol. 2001, 35, pp. 2583-2588.
Caprioli, Richard M. et al., "Molecular Imaging of Biological Samples: Localization of Peptides and Proteins Using MALDI-TOF MS", Anal. Chem. 1997, 69, pp. 4751-4760.
Bradshaw, Robert et al., "A Novel Matrix-Assisted Laser Desorption/Ionisation Mass Spectrometry Imaging Based Methodology for the Identification of Sexual Assault Suspects", Rapid Commun. Mass Spectrom. 2011, 25, pp. 415-422.
Strohalm, Martin et al., "mMass 3: A Cross-Platform Software Environment for Precise Analysis of Mass Spectrometric Data", Anal. Chem. 2010, 82, pp. 4648-4651.
Stoeckli, Markus et al., "Molecular Imaging of Amyloid β Peptides in Mouse Brain Sections Using Mass Spectrometry", Analytical Biochemistry 311 (2002) pp. 33-39.
Strohalm, Martin et al., "RCM Letter to the Editor", Rapid Communications in Mass Spectrometry, Rapid Commun. Mass Spectrom. 2008; 22: pp. 905-908.
Rowell, Frederick et al., "Detection of Drugs and Their Metabolites in Dusted Latent Fingermarks by Mass Spectrometry", Analyst, 2009, 134, pp. 701-707.
Aerni, Hans-Rudolf et al., "Automated Acoustic Maxtrix Deposition for MALDI Sample Preparation", Anal. Chem. 2006, 78, pp. 827-834.
Sloane et al., "High Throughput Peptide Mass Fingerprinting and Protein Macroarry Analysis Using Chemical Printing Strategies" Molecular Cellular Proteomics, Jul. 2002, Issue 1.7, pp. 490-499.
Francese et al., "Detection of Honey Bee Venon in Envenomed Tissue by Direct MALDI-MSI", J. Am. Soc. of Mass Spectrom, Sep. 2009, vol. 20, Issue 15, pp. 112-123.
Hankin et al., "Sublimation as a Method of Matrix Application for Mass Spectrometic Imaging", J. Am. Soc. of Mass Spectrom, Jun. 2007, vol. 18, Issue 14, pp. 1646-1652.
Puolitaival et al., "Solvent-Free Matrix Dry-Coating for MALDI Imaging of Phospholipids", J Am Soc Mass Spectrom, Feb. 2008, vol. 19, Issue 14, pp. 882-886.
PCT International Search Report for PCT/GB2012/050460, dated May 3, 2012, 4 pages.
Chaurand, Pierre et al., "Imaging Mass Spectrometry: A New Tool to Investigate the Spatial Organization of Peptides and Proteins in Mammalian Tissue Sections," Sep. 2002, pp. 676-681.
Ferguson, Leesa Susanne et al., "Direct Detection of Peptides and Small Proteins in Fingermarks and Determination of Sex by MALDI Mass Spectrometry Profiling", Analyst, 2012, 137, pp. 4686-4692.
Francese, Simona et al., "MALDI Mass Spectrometry Imaging, From Its Origins Up to Today: The State of the Art", Combinational Chemistry & High Throughput Screening, 2009, 12, pp. 156-174.

\* cited by examiner

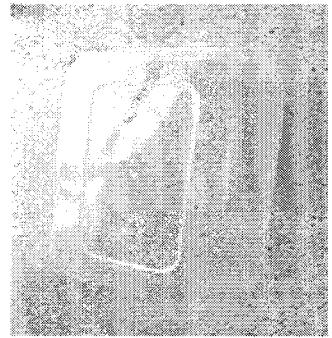
Fig. 8A  Fig. 8B  Fig. 8C  Fig. 8D  Fig. 8E

MATRIX ASSISTED LASER DESORPTION IONISATION MASS SPECTROMETRY IMAGING (MALDI-MSI)

RELATED APPLICATIONS

This application is the National Stage of International Patent Application No. PCT/GB2012/050460, filed on Mar. 1, 2012, which claims priority to and all the advantages of Great Britain Patent Application No. GB1104003.7, filed on Mar. 9, 2011, and Great Britain Patent Application No. GB 1104365.0, filed on Mar. 15, 2011, the contents of which are incorporated herein by reference.

The present invention relates to a method of preparing a sample for matrix assisted laser desorption ionisation mass spectrometry imaging (MALDI-MSI) and in particular, although not exclusively, a method of generating an image of the sample using mass spectrometry.

Matrix deposition is a crucial aspect in MALDI-MSI. Extensive research has been undertaken over the years to improve this preparation step with the aim of minimising analyte delocalisation while maximising the available resolution and analyte extraction from the tissue section. The selection of the most appropriate matrix and solvent combination impacts on the analyte extraction (sensitivity); nonetheless it is the choice of the deposition method that has, overall, a greater impact.

Minimisation of analyte delocalisation can be achieved not only by using appropriate sample pre-treatments but also by selecting a deposition method which either confines the matrix to a very small area (microspotting for example) or spraying the matrix either robotically or manually. Contactless microspotting can currently be achieved by piezo-dispensing the solution using a chemical ink-jet printer [1. Sloane, A. J.; Duff, J. L.; Wilson, N. L.; Gandhi, P. S.; Hill, C. J.; Hopwood, F. G.; Smith, P. E.; Thomas, M. L.; Cole, R. A.; Packer, N. H.; Breen, E. J.; Cooley, P. W.; Wallace, D. B.; Williams, K. L.; Gooley, A. A. *Mol Cell Proteomics* 2002, 1, 490-499] or through acoustic ejection first introduced as a prototype by Aerni and collaborators [Aerni, H. R.; Cornett, D. S.; Caprioli, R. M.; *Anal Chem,* 2006, 78, 827-834] and then improved and commercialised by Labcyte as the Portrait™ 630. Here both matrix concentration and solvents used to dissolve the matrix have an important role in determining the size of the crystallized droplet and the spot to spot distance, which determine the final image resolution. WO 2010/007443 describes a dual analysis technique that encompasses a more conventional non-imaging MALDI-MS chemical profile analysis but which also considers the affects of matrix particle size. A first stage is directed to obtaining an image of a deposited fingermark using a lifting agent and applying a developing agent. An image of the ridge pattern of the treated fingermark is then obtained using a solid-state or an optical fingerprint reader. A second stage chemical profiling analysis is then undertaken using MALDI MS involving dusting of the fingerprint sample with a silica nanoparticle powder using a commercial magnetic wand.

Pneumatically assisted matrix spray-coating, for which the first example was reported by Caprioli and collaborators [Caprioli, R. M.; Farmer, T. B.; Gile, J. *Anal Chem,* 1997, 69, 4751] requires the optimisation of the distance between the sample and the spray nozzle, deposition speed and number of coating layers (this generally depends on matrix solvent combinations).

The matrix can also be applied through a matrix aerosol created by vibrational vaporization that requires a number of parameters be monitored and optimised such as deposition time, intervals, matrix layer thickness, wetness and drying rate. This deposition system is claimed to generate a droplet size of 20 μm in diameter typically covering an area on the tissue smaller than 50 μm in diameter. This and the ability to control the relevant deposition parameters allow images with excellent spatial resolution and high ion intensity to be achieved.

For manual spray coating, it is important to find optimal conditions for the spray distance, number of cycles and elapsed time between consecutive spraying. Whichever the deposition method, it has an influence on the crystal formation in terms of speed (slow formation has been observed to yield higher intensity signal) and size, with the latter having a direct effect on the image resolution that will then only be limited by the laser spot diameter if oversampling is not performed. The deposition method can also affect the signal intensity as it can impact on the analyte extraction-matrix co-crystallisation. In terms of sample pre-treatment, immersion techniques involving dipping the mounted section in a bath of matrix solution prior to matrix deposition have been observed to increase the signal without delocalising the analyte [Stoeckli, M.; Staab, D.; Staufenbiel, M.; Wiederhold, K. H.; Signor L. *Anal Biochem,* 2002, 311, 33-39; Francese, S.; Lambardi D.; Mastrobuoni, G.; la Marca, G.; Moneti, G.; Turillazzi, S. *J Am Soc Mass Spectrom,* 2009, 20, 112-123]. Independently from the mode of application, the most widely used deposition methods involve the use of 'wet' matrix, i.e. dissolved in an appropriate solvent combination prior to deposition. Sugiura and collaborators used this principle in a two step procedure to deposit matrix over a tissue section [Sugiura, Y.; Shimma, S.; Setou, M. *Anal Chem,* 2006, 78, 8227]. The method named 'spray droplet', involved spray-coating the matrix in humid conditions and in low concentration (the seeding step) followed by microspotting matrix at a higher concentration using a chemical ink-jet printer. The control over iterative spray coating cycles and humidity made this procedure very efficient in terms of ion population (m/z range 4-20 kDa) and ion intensity compared to the single step conventional deposition method.

Although not fully embraced by the MALDI-MSI community, a number of other deposition methods have been shown to improve the ion intensity and to yield more populated mass spectra. These methods are based on the use of 'dry' matrix, which in most cases acts as a seeding agent. Aerni and co-workers were the first to report the use of ground matrix powder being brushed off a sample surface and subsequent matrix microspotting using an acoustic ejector [Aerni, H. R.; Cornett, D. S.; Caprioli, R. M.; *Anal Chem,* 2006, 78, 827-834]. Powder seeding prior to matrix microspotting yielded more homogenous matrix spots and smaller crystals and although it did not produce any ion signal without subsequent spotting, seeding greatly improved the total ion count (TIC) (m/z 5-8 kDa).

In 2007 Hankin and co-workers demonstrated that matrix powder could indeed be used to generate ions and ion images by sublimation and compared this method with conventional electrospray deposition [Hankin, J. A.; Barkley, R. M.; Murphy, R. C. *J Am Soc Mass Spectrom,* 2007, 18, 1646-1652]. In the new method, the dry matrix was sublimed under vacuum and required the optimisation of a range of parameters including pressure, condenser temperature, amount of matrix, heat applied to the matrix and sublimation time.

Although the method required laborious fine-tuning of all these parameters, it yielded a homogeneous coating and higher intensity phospholipid signals and corresponding distribution maps in sections of mouse brain. In 2008 Puolitaival and co-workers published the use of a solvent-free matrix dry coating method that allowed detection and mapping of phospholipids with a 30 μm to 100 μm lateral resolution [Puolitaival, S. M.; Burnum, K. E.; Cornett, D. S.; Caprioli R. M. *J Am Soc Mass Spectrom*, 2008, 19, 882-886]. In their work, the matrix was simply finely ground using a mortar and pestle and applied by using a 20 μm sieve. Although they did not directly compare the method with that of Hankin and collaborators, a comparison was made with a spray-coating method using a TLC nebuliser. Whereas the quality of the molecular images and the phospholipid localisation were very similar to those achieved with the spray-coating, the authors claimed simplicity of sample preparation and minimisation of the analyte delocalisation as advantages of their method over the classical one. This method has been successfully used later to map and quantify small molecules by Goodwin and collaborators [Goodwin, R. J.; MacIntyre, L.; Watson, D. G.; Scullion S. P.; Pitt A. R.; *Rapid Commun. Mass Spectrom*, 2010; 24: 1682-1686; Goodwin, R. J.; Scullion, P.; MacIntyre, L.; Watson, D. G.; Pitt, A. R. *Anal Chem*, 2010, 1751-61].

The very nature of latent fingermarks, being fingermarks with low sample volume and invisible to the naked eye, means that they cannot be analysed via MALDI-MSI without the fingermark being in some way enhanced initially. If conventional processes are to be taken as suitable starting points, the enhancement process would need to be compatible with the MALDI-MSI analysis and the fingermark recovered and laid on a flat and thin surface (less than 200 μm—typically suitable for MALDI-MSI analysis) for instrumental analysis.

Currently employed enhancement methods can be categorised as optical, physical, physico-chemical or chemical, commonly used examples of each being UV light, black powder, cyanoacrylate fuming and ninhydrin, respectively. The Home Office Scientific Development Branch (HOSDB) publish the Manual of Fingerprint Development Techniques based on their research and testing. [Bowman, V.; *Manual of fingerprint development techniques, $2^{nd}$ ed.*; Police Scientific Development Branch, Home Office, Sandridge, UK, 2004]. The manual details the techniques that have been approved for operational use and the order in which they should be applied for a specific set of conditions (primarily surface type and contact with water). The processing flow charts are organised at the first level by the type of surface on which the fingermark is deposited: smooth non-porous, rough non-porous, paper and cardboard, plastics, metal, raw wood, adhesive coated surfaces etc. This necessarily means that the choice of enhancement technique depends largely on the type of deposition surface rather than the chemical composition of the fingermark in question.

What is required is a method of preparing a MALDI-MSI sample suitable for introduction into a MALDI mass spectrometer that is largely independent of the surface or substrate material upon which the sample is deposited. Additionally, there is a need for an improved analytical method for recovering fingermarks from a crime scene and enabling crime scene-remote (laboratory) analysis. Importantly, the sample recovery and preparation method must preserve the fingermark characteristics to enable remote analysis.

Accordingly, the inventors provide a method of preparing a mass spectrometry imaging sample via a two-step sample preparation procedure, referred to herein as the 'dry-wet method'. Using the two-step preparation procedure of powdering and then spraying a matrix soluble solvent on to the fingermark for efficient analyte extraction and co-crystallisation, a superior procedure is achieved over the pneumatically assisted matrix spray coating in particular for fingermark analysis by MALDI-MSI. Moreover, the present dry-wet method has proved to be reproducible and advantageous over conventional spray coating deposition, in terms of preparation time and recording of the evidence prior to MALDI-MSI analysis.

The present method of preparing the sample allows fingermark recovery from a deposition surface whilst preserving the sample integrity and characteristics to enable an accurate image and chemical information to be obtained. When trialled on fingermarks deposited on aluminium surfaces, the present method is superior to the conventional spray coating method in terms of quality of the fingermark mass spectrometric image and ion intensity. The present method is also, to a large extent, insensitive to the substrate material upon which the fingermark/sample is deposited. In particular, the dry-wet method allows images of latent fingermarks to be obtained after recovery from a variety of different surfaces including porous and non-porous surfaces such as, by way of example only, glass, metal, plastic, wood and leather.

Additionally, the inventors have demonstrated that ungroomed fingermarks (fingermarks with very low amounts of sebaceous compounds) can be analysed to obtain both chemical information and good quality ridge pattern images. The present method therefore is highly sensitive and provides a versatile MALDI-MSI tool that may be integrated with standard operational procedures in the forensic analysis of latent fingermarks. The dry-wet method bridges the gaps between visualizing and recovering a latent fingermark at the crime scene and analysing it by MALDI-MSI as the matrix acts as a dusting (and therefore) enhancing agent.

According to a first aspect of the present invention there is provided a method of preparing a matrix assisted laser desorption ionisation mass spectrometry imaging (MALDI-MSI) sample comprising: dusting a sample with a MALDI-MSI matrix powder; removing excess matrix powder from the sample; spraying the dusted sample with a solvent in which both the matrix powder and the sample are soluble.

Preferably, the sample is a fingermark and in particular a latent fingermark. The present method is particularly suitable for MALDI-MSI analysis of fingermarks that have been lifted from a substrate surface upon which the fingermark has been initially deposited using an adhesive backed strip, pad or tape. In particular, the strip, pad or tape may be crime scene investigation (CSI) tape.

Preferably, the step of spraying the dusted sample comprises spraying the sample adhered to the strip, pad or tape with the solvent. Preferably, the method further comprises introducing the lifted sample on the strip, pad or tape into a MALDI mass spectrometer with imaging capabilities so as to obtain an image of the sample by MALDI-MSI. Preferably the strip, pad or tape is adhered to a MALDI target plate prior to introduction into the MALDI mass spectrometer.

Preferably, the particle size of the powered matrix is in the range 5 μm to 120 μm. More preferably, the powered matrix is in the range 10 μm to 30 μm. Preferably, the matrix is an absorber of UV radiation and/or is fluorescent. It has been identified that a decrease in the particle size of the matrix employed leads to an increase of the mass spectrometric fingermark image quality.

Preferably, the step of spraying the dusted sample comprises spraying the solvent onto the dusted sample (and optionally the lifted sample on the adhesive backed strip, pad or tape), as a fine mist. Preferably, the method comprises three successive spray applications of the fine mist onto the sample. Preferably, the method comprises creating the fine mist using an automatic pneumatic sprayer device. Preferably, the spray speed is in the range 1 to 3 μL/min and preferably 2 μL/min.

According to a second aspect of the present invention there is provided a method of matrix assisted laser desorption ionisation mass spectrometry imaging (MALDI-MSI) comprising preparing a sample as described herein; introducing the sample into a MALDI mass spectrometer with imaging capabilities; delivering a laser beam to the sample within the mass spectrometer; and generating at least one image of the sample.

According to a third aspect of the present invention there is provided a method of creating a plurality of images of a fingermark comprising: preparing a sample as described herein; introducing the prepared sample into a MALDI mass spectrometer with imaging capabilities; obtaining at least one image of the fingermark using the imaging mass spectrometer.

Preferably, the method further comprises obtaining a fluorescent image of the prepared sample using a fluorescent microscope. More preferably, the method further comprises obtaining a UV image of the prepared sample using a UV light source and a still and/or video camera.

A specific implementation of the present invention will now be described, by way of example only and with reference to the accompanying figures in which.

Figure 3:
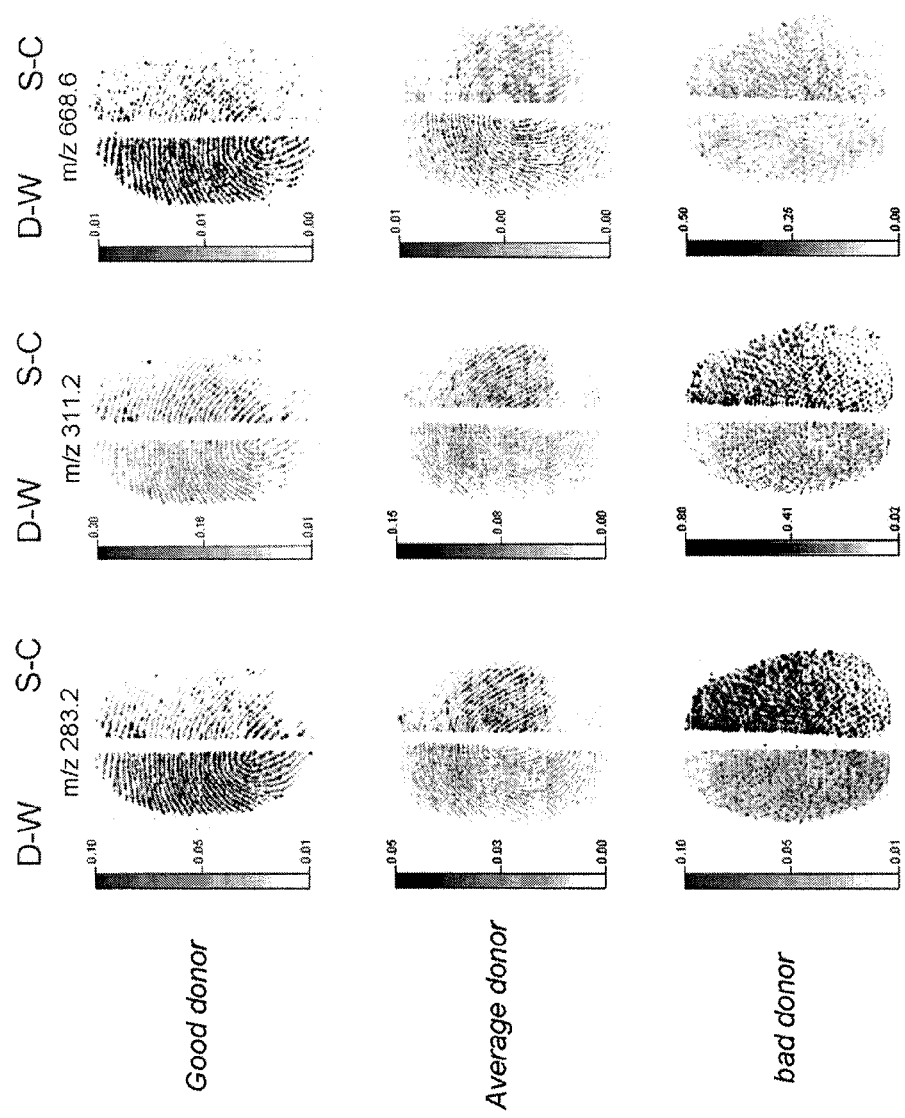

FIG. 3 illustrated the MALDI MSI analysis of fingermarks prepared with either the Dry-Wet (D-W) or the Spray Coating (S-C) matrix application method. Three types of donors have been selected and three ions were imaged at m/z 283.2, 311.2 and 668.6 both within the fingermarks' halves prepared with the dry-wet method and for the halves prepared with the spray coating matrix application method.

Figure 4:
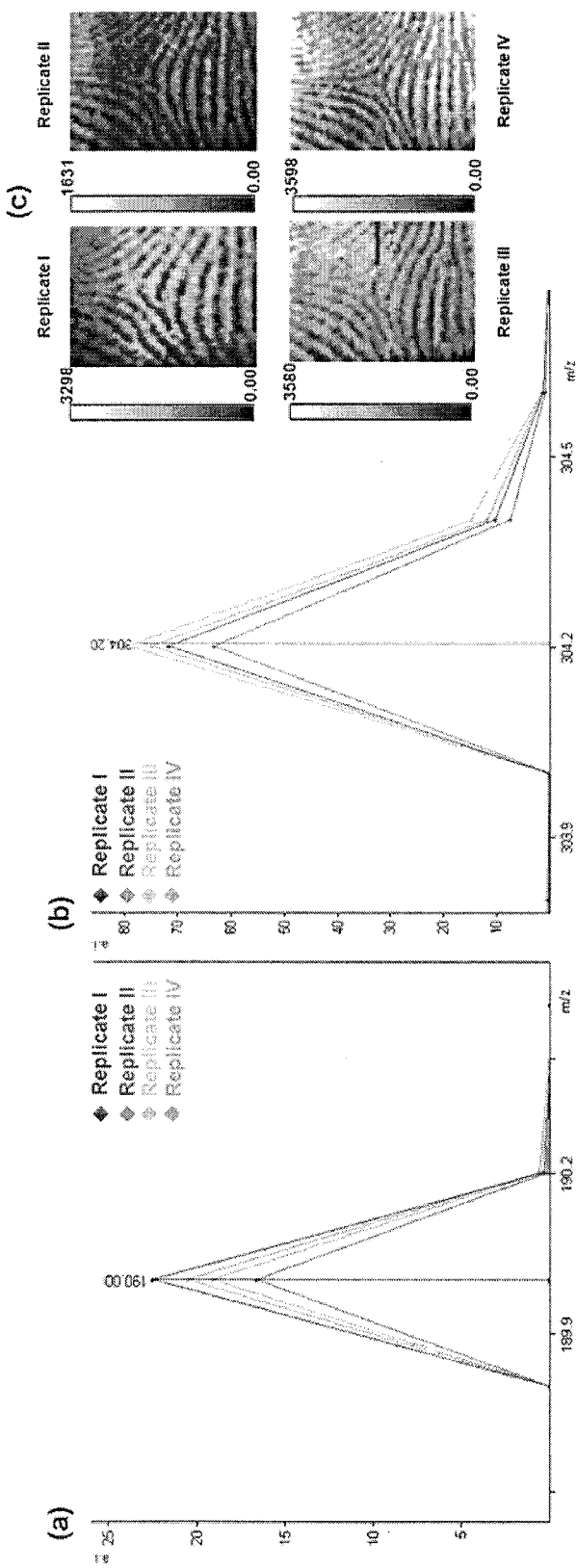
Figures 5A, 5B, 5C, 5D, 5E:
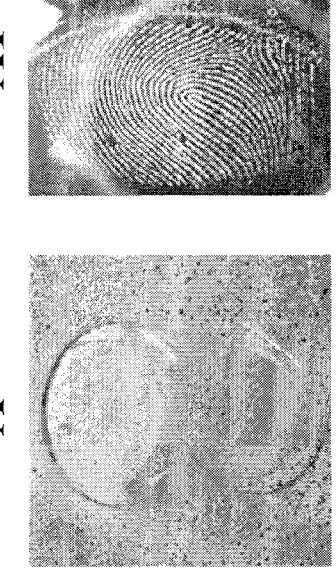
Figures 6A, 6B, 6C, 6D, 6E:
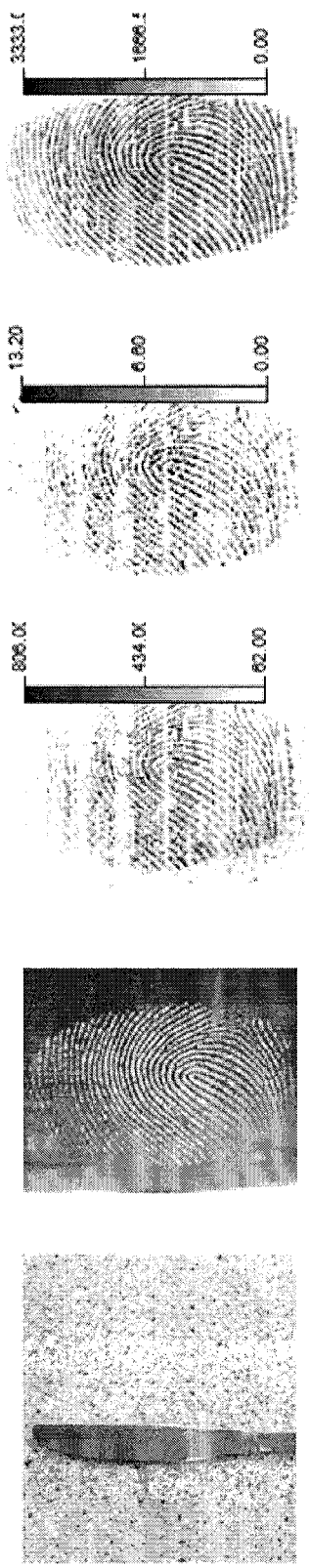
Figures 7A, 7B, 7C, 7D, 7E:
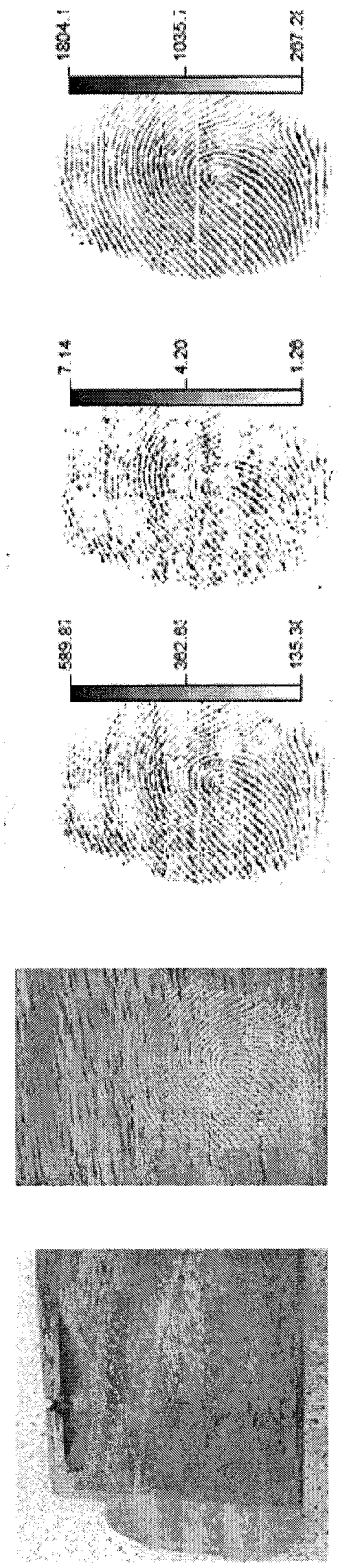
Figures 9C, 9D, 9E:
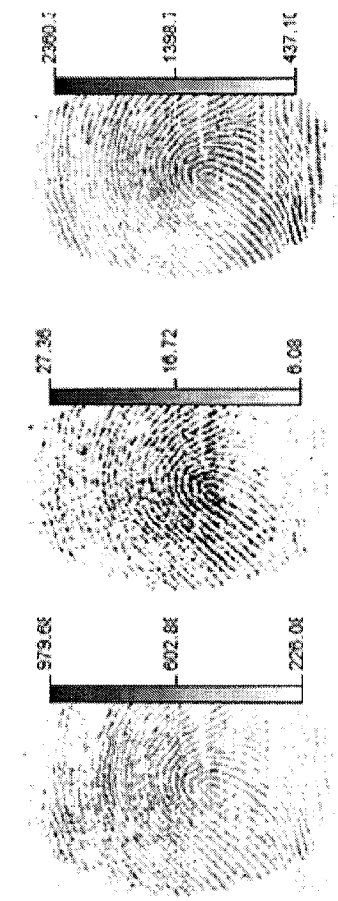
Figure 9B:
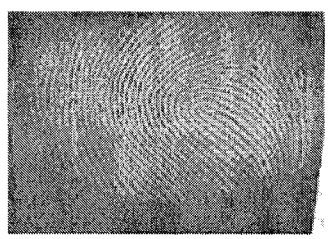
Figure 9A:
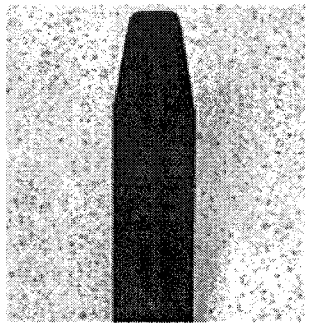
Figure 10:
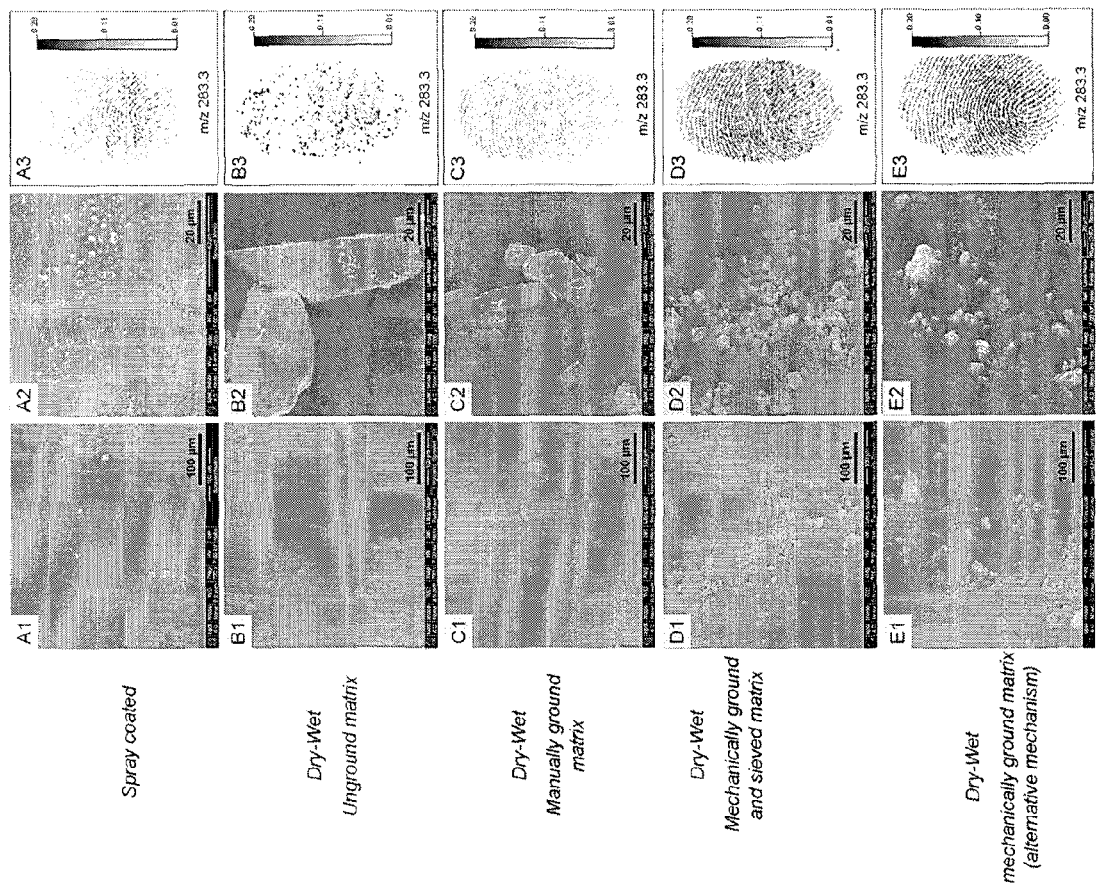

FIG. 4 illustrates the superimposition of a α-CHCA ion signal at m/z 190 (a) from four finger marks deposited independently and prepared using the present two-stage preparation method; an exogenous signal at m/z 304 (dimethylbenzylammonium ion) also produced superimposable spectra (b); and detail of the corresponding four MALDI MS images of the ion at m/z 304 is illustrated in (c);

FIG. 5A is a photograph of an ungroomed fingermark deposited on a glass beaker;

FIG. 5B is a photograph of the fingermark deposited on the glass beaker of FIG. 5A dusted with the MALDI matrix (α-CHCA);

FIG. 5C is a MALDI-MSI image of the fingermark of FIG. 5B having been lifted from the beaker with an adhesive backed tape and sprayed with an appropriate solvent followed by MALDI-MSI analysis to provide an image of an endogenous amino acid (putative lysine m/z 147);

FIG. 5D is a MALDI-MSI image of the fingermark of FIG. 5B lifted, prepared and analysed in the same manner as FIG. 5C to provide an image of an endogenous fatty acid (oleic acid m/z 283);

FIG. 5E is a MALDI-MSI image of the fingermark of FIG. 5B lifted, prepared and analysed in the same manner as FIG. 5C to provide an image of an exogenous compound (dimethylbenzylammonium ion m/z 304);

FIG. 6A is a photograph of an ungroomed fingermark deposited on a metal knife;

FIG. 6B is a photograph of the fingermark deposited on the metal knife of FIG. 6A dusted with the MALDI matrix (α-CHCA);

FIG. 6C is a MALDI-MSI image of the fingermark of FIG. 6B having been lifted from the metal knife with an adhesive backed tape and sprayed with an appropriate solvent followed by MALDI-MSI analysis to provide an image of an endogenous amino acid (putative lysine m/z 147);

FIG. 6D is a MALDI-MSI image of the fingermark of FIG. 6B lifted, prepared and analysed in the same manner as FIG. 6C to provide an image of an endogenous fatty acid (oleic acid m/z 283);

FIG. 6E is a MALDI-MSI image of the fingermark of FIG. 6B lifted, prepared and analysed in the same manner as FIG. 6C to provide an image of an exogenous compound (dimethylbenzylammonium ion m/z 304);

FIG. 7A is a photograph of an ungroomed fingermark deposited on wood;

FIG. 7B is a photograph of the fingermark deposited on the wood of FIG. 7A dusted with the MALDI matrix (α-CHCA);

FIG. 7C is a MALDI-MSI image of the fingermark of FIG. 7B having been lifted from the wood with an adhesive backed tape and sprayed with an appropriate solvent followed by MALDI-MSI analysis to provide an image of an endogenous amino acid (putative lysine m/z 147);

FIG. 7D is a MALDI-MSI image of the fingermark of FIG. 7B lifted, prepared and analysed in the same manner as FIG. 7C to provide an image of an endogenous fatty acid (oleic acid m/z 283);

FIG. 7E is a MALDI-MSI image of the fingermark of FIG. 7B lifted, prepared and analysed in the same manner as FIG. 7C to provide an image of an exogenous compound (dimethylbenzylammonium ion m/z 304);

FIG. 8A is a photograph of an ungroomed fingermark deposited on plastic;

FIG. 8B is a photograph of the fingermark deposited on the plastic of FIG. 8A dusted with the MALDI matrix (α-CHCA);

FIG. 8C is a MALDI-MSI image of the fingermark of FIG. 8B having been lifted from the plastic with an adhesive backed tape and sprayed with an appropriate solvent followed by MALDI-MSI analysis to provide an image of an endogenous amino acid (putative lysine m/z 147);

FIG. 8D is a MALDI-MSI image of the fingermark of FIG. 8B lifted, prepared and analysed in the same manner as FIG. 8C to provide an image of an endogenous fatty acid (oleic acid m/z 283);

FIG. 8E is a MALDI-MSI image of the fingermark of FIG. 8B lifted, prepared and analysed in the same manner as FIG. 8C to provide an image of an exogenous compound (dimethylbenzylammonium ion m/z 304);

FIG. 9A is a photograph of an ungroomed fingermark deposited on leather;

FIG. 9B is a photograph of the fingermark deposited on the leather of FIG. 9A dusted with the MALDI matrix (α-CHCA);

FIG. 9C is a MALDI-MSI image of the fingermark of FIG. 9B having been lifted from the leather with an adhesive backed tape and sprayed with an appropriate solvent followed by MALDI-MSI analysis to provide an image of an endogenous amino acid (putative lysine m/z 147);

FIG. 9D is a MALDI-MSI image of the fingermark of FIG. 9B lifted, prepared and analysed in the same manner as FIG. 9C to provide an image of an endogenous fatty acid (oleic acid m/z 283);

FIG. 9E is a MALDI-MS image of the fingermark of FIG. 9B lifted, prepared and analysed in the same manner as FIG. 9C to provide an image of an exogenous compound (dimethylbenzylammonium ion m/z 304);

FIG. 10 illustrates the comparative analysis via SEM and MALDI MSI of fingermarks prepared with the spray coat and the dry-wet methods. Panels A1-D1 report a 700× magnification image of the dusted fingermarks with the spray coat (S-C) and the dry-wet (D-W) methods and different particle size (A1=S-C method, B1=D-W method and unground matrix, C1=D-W method and manually ground matrix, D1=D-W method and mechanically ground and sieved matrix). Panels A2-D2 show a 3000× magnification of panels A1-D1. Panels A3-D3 show the corresponding MALDI MS images of distribution on the entire fingermark of the ion at m/z 283.2.

The present MALDI-MSI preparation method comprises a relatively straight forward two-stage procedure involving a first dusting of the sample with powered matrix followed by spraying of the dusted sample with a matrix compatible solvent. Importantly, the present process enables samples with low abundance substances, such as fingermarks, to be analysed by mass spectrometry imaging. The present method is also advantageous in that sample fingermarks can be lifted from the substrate upon which they were deposited allowing subsequent and remote (laboratory) analysis.

Furthermore, through experimental testing, the inventors have confirmed the enhanced sensitivity of the present method being suitable to generate very detailed and accurate mass spectrometry images for latent fingermarks having low concentrations of endogenous and exogenous constituent compounds deposited on a substrate. Such fingermarks are referred to as 'ungroomed' where 'groomed' fingermarks typically contain higher levels of endogenous sebaceous compounds that result from an individual wiping fingertips over their skin prior to deposition on a substrate. Accordingly, the quality and reproducible results for 'ungroomed' fingermarks confirm the suitability of the present method for actual crime scene analysis where fingermark samples would typically contain minimal material.

The inventors also demonstrate the advantages of the present method over the conventional spray coat method for the analysis of fingermark samples deposited on a variety of different substrate surfaces having different properties including, in particular, porosity and surface roughness. Example substrates tested include glass, metal, plastic, wood and leather. The results obtained confirm the suitability of the present method to lift fingermarks from different substrate surfaces with little or no loss of image clarity.

Furthermore, chemical analysis of the lifted fingermark samples is also possible with the present method enabling the identification of both endogenous and exogenous compounds. This is indeed a significant contribution to current forensic analysis as it is now possible to firstly identify and then extract very low quantities of biological samples at a crime scene that may have otherwise been undetected and to obtain both an image and a chemical breakdown of the sample.

Experimental
Materials

Trifluoroacetic acid (TFA), α-cyano-hydroxycinnamic acid (CHCA) and ALUGRAM® SIL G/UV$_{254}$ pre-coated aluminium sheets were purchased from Sigma Aldrich (Poole, UK). Acetone and aceonitrile (ACN) were obtained from Fisher Scientific (Loughborough, UK). MALDI target OPTI spotless inserts were purchased from Applied Biosystems (CA, USA). Double sided conductive carbon tape was obtained from TAAB (Aldermaston, UK). Klenair air spray was obtained from Kenco Ltd (Swindon, UK). Dettol alcohol wipes were purchased from Sheffield branches of Wilkinson's (Worksop, UK). Forensic lifting tape was acquired from TETRA Scene of Crime (http://www.tetrasoc.com/).

Instrumentation

MALDI MS Imaging analyses were conducted using a modified Applied Biosystems API Q-Star Pulsar i hybrid quadrupole time-of-flight (QTOF) instrument. The orthogonal MALDI source has been modified to incorporate a SPOT 20 kHz Nd:YVO4 solid-state laser (Elforlight Ltd., Daventry, UK), having a wavelength of 355 nm, a pulse duration of 1.5 ns and producing an elliptical spot size of 100 μm×150 μm. Images were acquired using 'oMALDI Server 5.1' software supplied by MDS Sciex (Concord, Ontario, Canada). High mass accuracy MALDI MS spectra were acquired directly from fingermarks using a SYNAPT G2-HDMS™ system incorporating ion mobility (Waters, Manchester, UK) operating in resolution mode ("V"). The laser was operated at 1 kHz, which equates to a laser energy of approximately 10.5 μJ. Latent fingermarks were sprayed using a 'SunCollect' autospraying system obtained from SunchromGmbH (Friedrichsdorf, Germany). All Scanning Electron Microscopy (SEM) images were obtained using a FEI NOVA nanoSEM 200 (FEI, The Netherlands) fitted with a HELIX bullet/detector system to enable electron imaging in variable pressure (VP) mode.

Methods
Fingermark Preparation

Ungroomed fingermarks were prepared by preliminarily cleaning hands with alcohol wipes and carrying on normal work activities for a period of 15 minutes before deposition. The marks were laid onto the ALUGRAM® SIL G/UV$_{254}$ pre-coated aluminum sheets after scraping off the silica with acetone. Ungroomed fingermarks were also deposited on a knife (metal, non porous surface), an air tight plastic container (non porous surface) a laboratory beaker (glass, non porous surface), a wood tray (varnished wood) and a belt (leather, porous surface).

Application of Matrix

Using a pestle and mortar, α-CHCA was ground into a very fine powder, which was used to dust the fingermark using a zephyr brush. Approximately 40 mg to 70 mg of matrix was found suitable for dusting a fingermark of approximate size 2 cm×1.3 cm. Excess powder was then removed using a Klenair air sprayer. The aluminium sheet with the dusted fingermark on it was then stuck onto a MALDI spotless 'OPTI-Tof™', insert using double sided conductive carbon tape and sprayed with 3 layers of a 70:30 ACN/0.5% TFA solution using the SunCollect auto-sprayer, at a speed of 2 μL/min. Fingermarks deposited on the different surfaces employed were dusted and lifted with crime scene investigation (CSI) tape. The tape was then stuck using double sided conductive carbon tape onto a MALDI spotless insert and then sprayed in the same fashion with 3 layers of 70:30 ACN/0.1% solution.

When comparing the Dry-Wet method with the conventional Spray Coating matrix application method, ungroomed fingermarks obtained from 3 donors (a good, intermediate and poor secretor) were laid onto aluminum plates. For each donor fingermarks were divided in halves. When using the dry-wet method, one half was dusted with mechanically ground α-CHCA using a zephyr brush and excess powder was blown off prior to auto-spaying the sample with 5 layers of a 70:30 ACN/0.5% TFA solution at a speed of 5 µL/min. The other half of each donors' fingermark was prepared by auto-spraying with 4 layers of a 5 mg/ml α-CHCA in a 70:30 ACN/0.1% solution using the SunCollect auto-sprayer at a speed of 1 µL/min, 2 µL/min, 2 µL/min and 2 µL/min. Both methods had been previously optimised to provide the best quality image of the fingermark.

For comparative analyses via SEM and MALDI MSI, the fingermarks were dusted using a zephyr brush with either unground α-CHCA, manually ground α-CHCA (ground into a fine powder using a pestle and mortar) or mechanically ground α-CHCA using a Herzog vibrating disc mill (Herzog, Osnabruck, Germany) and sieved through a 38 µm sieve or a PM100 Planetary Ball Mill (Retsch Ltd Castleford, UK). Excess powder was then removed using a Klenair air sprayer. Fingermarks were sprayed with 5 layers of a 70:30 solution of ACN/0.5% TFA, at a rate of 5 µL/min prior to SEM and MALDI MSI analyses.

MALDI-TOF-MSI and HRMS Analyses

MALDI-TOF-MSI analyses were performed at a resolution of 150 µm×150 µm using 'continuous raster imaging' at a laser repetition rate of 5 kHz. This differs from the classic 'stop and go fashion' of MALDI-MSI, as the laser moves continuously in rows across the sample surface allowing rapid acquisition at a high image resolution. Images of a whole fingermark were obtained in around 1 h 20 min. Data processing was performed using BioMap 3.7.5 software (Novartis, Basel, Switzerland). High mass accuracy spectra were recorded directly from fingermarks prepared by the dry-wet method. Spectra were initially calibrated using a standard solution of polyethylene glycol (PEG), using the PEG signal at a m/z of 525.2886 as a lock mass and centroided prior to generation of an accurate peak list. The centroided m/z values were then submitted into the Lipidmap database (http://www.lipidmaps.org) using a mass tolerance of 0.001 Da in order to generate a list of probable structures.

Photography of the Fingermark Evidence

Digital images were obtained using a Fujifilm IS Pro CCD camera, with a 50 mm UV lens. The size of the image obtained was 4256×2848 pixels.

Fluorescence Visualisation of Fingermarks

UV-Vis and fluorescent images of fingermarks, prepared with the dry-wet method, were obtained using: (i) a video spectral comparator (VSC4CX, Foster & Freeman, Evesham, UK) at an excitation wavelength of 365 nm, (ii) using an Olympus BX51 fluorescent microscope equipped with Cell-D software (Olympus), using U-MNU2 filter (excitation 360-370 nm, 400 nm dichromatic, emission 420 nm) and (×4) objective.

Scanning Electron Microscopy (SEM)

All SEM images were acquired using an accelerating voltage of 5 KV, a spot size between 3-4 and at a working distance of 4-5 mm. Samples were examined at a magnification of ×700 and ×3000.

Overview

Specifically, a novel two step matrix deposition method (referred to herein as the 'dry-wet' method) has been devised and applied to the analysis of latent fingermarks. The first step involves the application of finely ground MALDI matrix to the fingermark, in this case α-cyano 4 hydroxycinnamic acid (α-CHCA). Molecular sieves, as indicated by Puolitaval and co-workers [Puolitaival, S. M.; Burnum, K. E.; Cornett, D. S.; Caprioli R. M. *J Am Soc Mass Spectrom,* 2008, 19, 882-886], were initially tested but their use was later dismissed as filtering the matrix in such a way proved to be very laborious and time consuming, with no significant improvement in the results obtained as well as being impractical for vertical surfaces. Additionally, dusting fingermarks is one of the conventional methodologies used by forensic investigators to develop marks at the crime scene, therefore, if introduced, this would be a familiar procedure for CSI officers. The second step involves the spraying of the matrix dissolution solvent.

Results

Figure 1B:
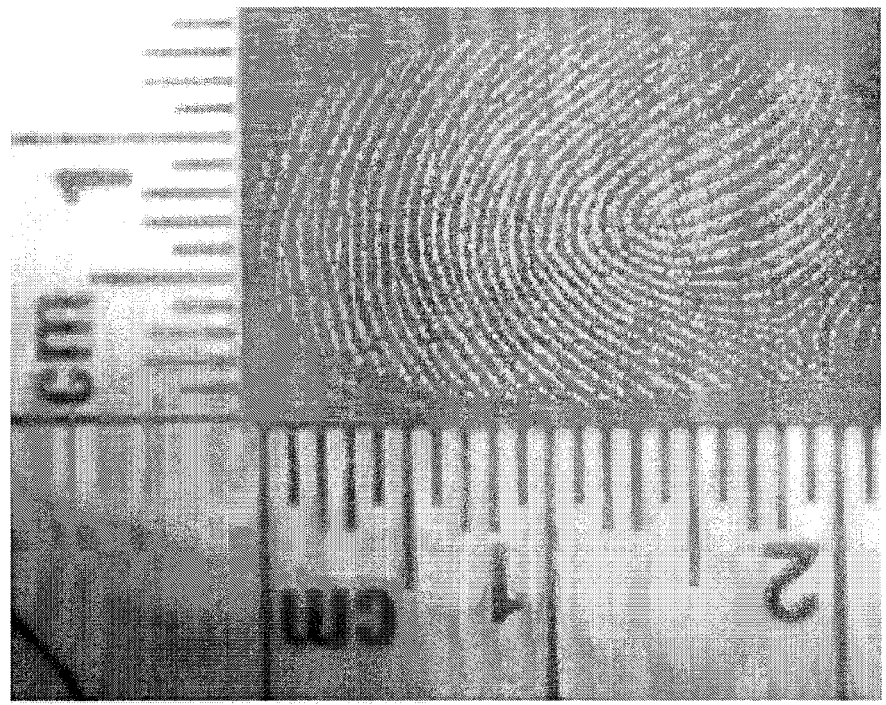
FIG. 1B illustrates the fingermark of FIG. 1A dusted with a MALDI matrix (α-CHCA)
Figure 1A:
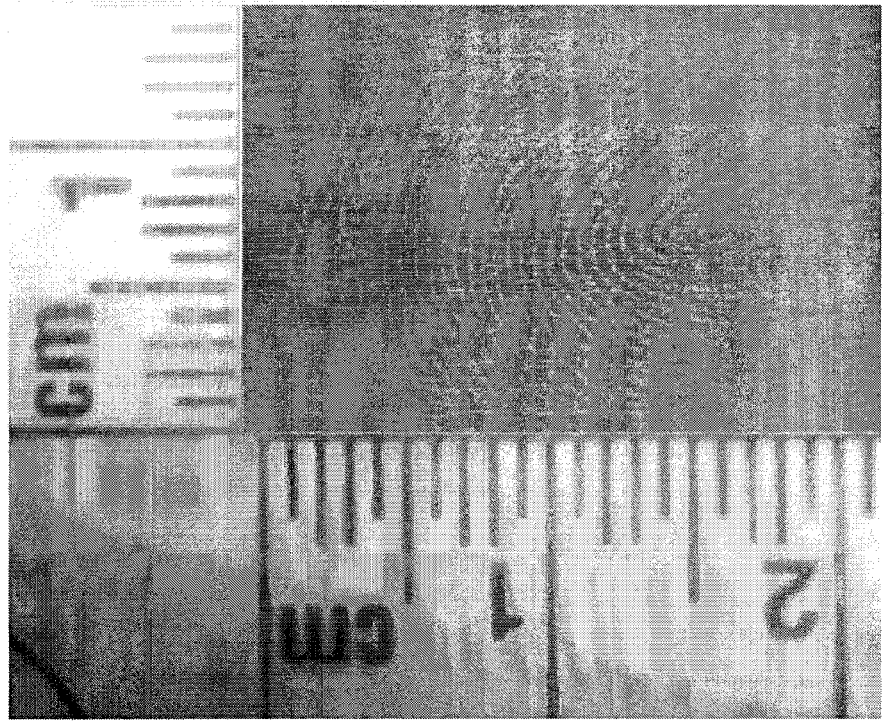
FIG. 1A is a non-enhanced visible light photograph of a latent fingermark present at a simulated crime scene.

In the first step of the method, the provided matrix acts as an enhancer and after blowing away excess, a photograph can be taken, as show in FIG. 1A. This may then be sent to a laboratory for scanning and comparison using police databases. FIG. 1A is a photograph of the fingermark prior to matrix dusting. After matrix application, a very clear ridge pattern is visualised (as illustrated in FIG. 1B) where the minutiae (local features of the ridge pattern) can be very clearly observed. According to the HOSDB grading system, where the proportion of the developed fingermark with clear ridge detail is estimated and a score is assigned to the fingermark from 0 to 4, the fingermark could be classified as grade 4 (full development—whole fingermark in clear continuous ridges). Another interesting aspect to this protocol is due to the αCHCA matrix having a fluorescent property. Accordingly, fluorescent optical images can be obtained either as a whole as shown in FIG. 1C, using a simple device like a document examination instrument operated at a wavelength of 365 nm, or as small areas, as shown in FIG. 1D, when using a fluorescent microscope operated as described in the methods. The magnification employed on the fluorescent microscope (40×) allowed the fingermark to be inspected with a high level of detail.

Figure 1E:
FIG. 1E is a MALDI-MSI image of the fingermark of FIG. 1B.
Figure 1D:
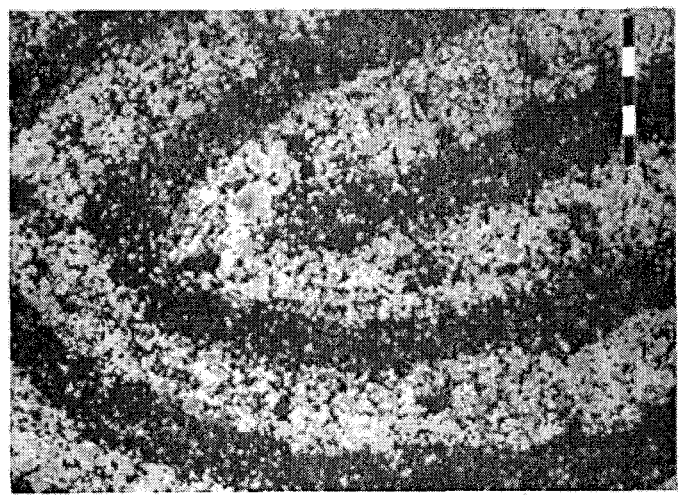
FIG. 1D is fluorescent microscopy image of the region of the fingermark as indicated in FIG. 1C.
Figure 1C:
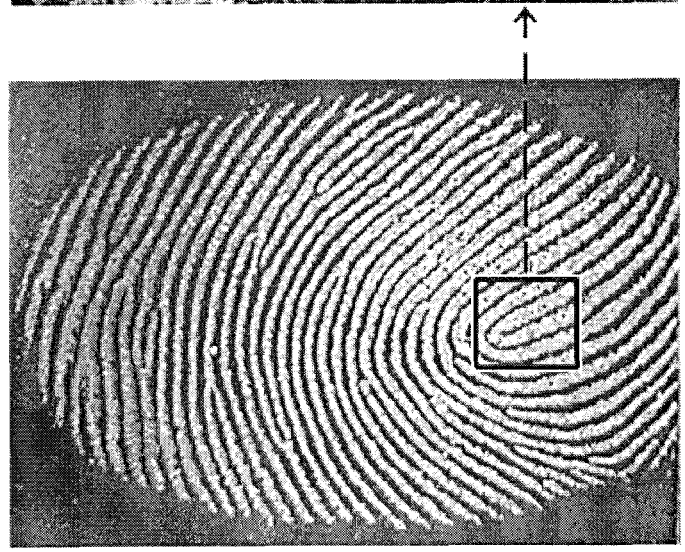
FIG. 1C illustrates a UV photograph of the MALDI matrix dusted fingermark of FIG. 1B.

The same fingermark may then be subjected to MALDI-MSI allowing the ridge pattern to be imaged simultaneously to potentially obtaining chemical information from the endogenous and exogenous compounds present in the fingermark as shown in FIG. 1E. The potential to acquire two different optical images prior to MALDI-MSI analysis is very important as it enables evidence to be provided quickly and according to existing and accepted forensic procedures. The concept of a multipurpose dusting agent has been reported by Rowell and co-workers [Rowell, F.; Hudson, K.; Seviour, J. *Analyst,* 2009, 134, 701-7]. These researchers employed a hydrophobic silica dusting agent containing carbon black which enabled both visualization and SALDI TOF MS analysis of the latent fingermarks. The chemical was a particularly good SALDI matrix targeting a range of drugs. Although chemical information could be obtained, SALDI TOF MS was not shown to provide a chemical image of the actual fingermark to complement the optical one. The dry-wet method allows the qualitative recovery of chemical information embedded in multiple MS images.

Figure 2A:
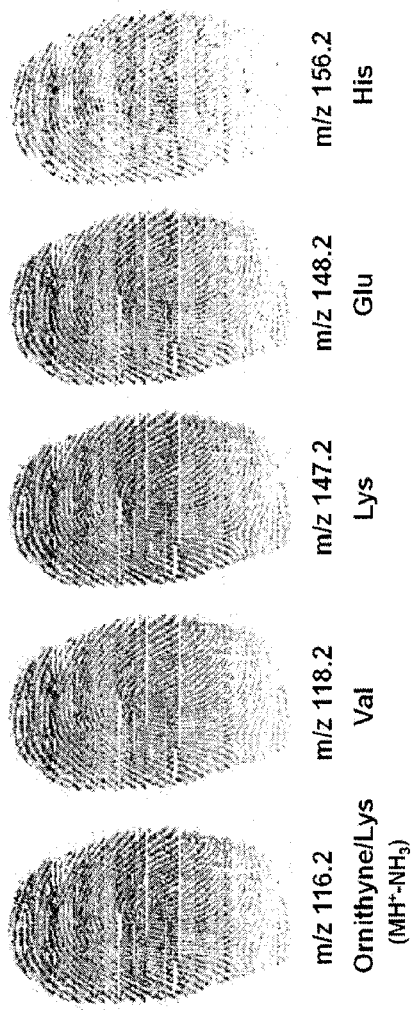
FIG. 2A is a series of MALDI-MS images of endogenous putative amino acids in an ungroomed fingermark prepared and analysed according to the present two-stage process.
Figure 2B:
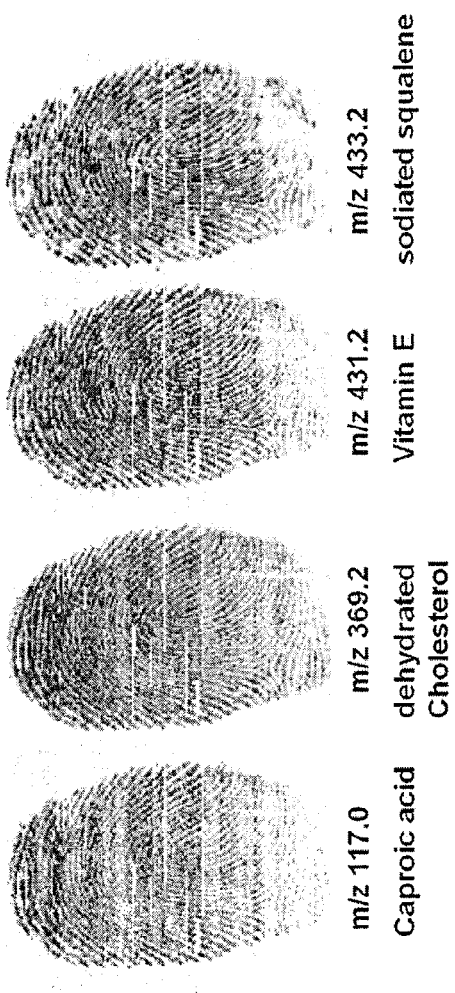
FIG. 2B is a series of MALDI-MS images of putative endogenous fatty acids and vitamins in the same ungroomed fingermark of FIG. 2A prepared and analysed according to the present two-stage process.
Figure 2C:
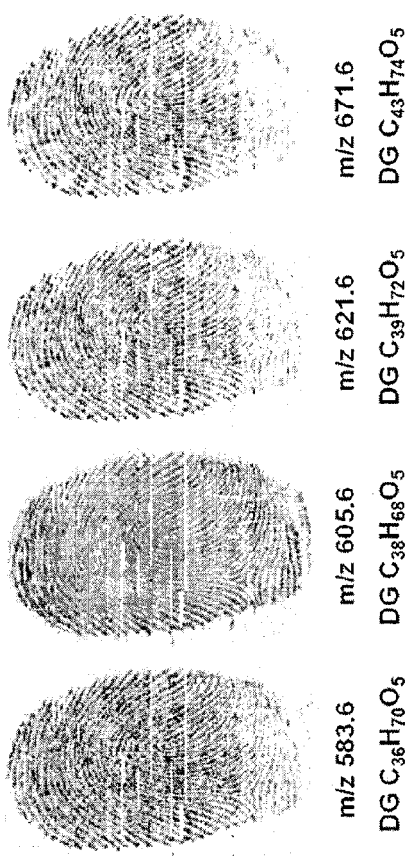
FIG. 2C is a series of MALDI-MS images of endogenous putative diacylglycerols in the same ungroomed fingermark of FIG. 2A prepared and analysed according to the present two-stage process.
Figure 2D:
FIG. 2D is a series of MALDI-MS images of endogenous putative triacylglycerols in the same ungroomed fingermark of FIG. 2A prepared and analysed according to the present two-stage process.

The dry-wet method devised allows images of fingermarks to be obtained showing detection of many molecular species, comparable to those previously reported by spray-coating the matrix [Wolstenholme, R.; Bradshaw, R.; Clench, M. R.; Francese, S. *Rapid Common Mass Specirom,* 2009, 23, 3031]. FIG. 2A illustrates the mapping of different putative amino acids including in particular: ornithyne/MH$^+$—NH$_3$ (at m/z 116.2); Val (at m/z 118.2); Lys (at m/z 147.2); and His (at m/z 156.2). FIG. 2B illustrates the mapping of a variety of different endogenous fatty acids and vitamins including in particular: Caproic acid (at m/z 117.0), dehydrated Cholesterol (at m/z 369.2), Vitamin E (at m/z 431.2) and sodiated squalene (at m/z 433.2). Furthermore, putative endogenous diacylglycerols were mapped including DG $C_{36}H_{70}O_5$ (at m/z 583.6), DG $C_{38}H_{68}O_5$ (at m/z 605.6), DG $C_{39}H_{72}O_5$ (at m/z 621.6) and DG $C_{43}H_{74}O_5$ (at m/z 671.6) as shown in FIG. 2C. Furthermore, and as shown in FIG. 2D a range of endogenous putative tricylglycerols were mapped from ungroomed fingermarks including in particular: triacyl-sn-glycerol (at m/z 174.0), TG $C_{58}H_{100}O_6$ (at m/z 893.8) and TG $C_{65}H_{122}O_6$ (at m/z 999.8). This is a particularly important advantage of the present method as it shows the versatility of MALDI-MSI compared to other currently used forensic technologies that need to be selected according to the molecular target.

When the particular distribution of a certain species is of interest (for example illicit substances) on an absolute scale or in relation to other substances, images would need to be normalised and the same contrast/brightness should be applied. Where the aim is obtaining an image that shows clear ridge pattern details for a fingermark area that is as large as possible, presence of a particular compound, rather than relative amounts, can be detected in an image by skipping the normalisation process if this reduces the number of minutiae retrievable.

The dry wet method was probed for its ability to provide high intensity signals and high quality images of fingermarks in a comparison with the conventional matrix spray coating. The comparison was made for three donors who were previously classified as good, average and bad secretors in order to evaluate robustness of the method. The classification, which generally applies to all the individuals, refers to the different ability to secret sweat which makes the ridge pattern detail of fingermarks more or less clear. In order to keep the experimental variables at a minimum level, the same donor's fingermark was divided in halves with one half prepared using the dry wet method and the other half by using the spray coating method. As a representative sample, the ion species were imaged at m/z 283.2, 311.2 and 668.6. The images were normalised against the total ion current; this does not always produce the best quality of the ridge detail. However, normalisation of the two differentially prepared fingermarks halves enables a more reliable comparison and observation of the distribution of the selected endogenous species. As it can be observed in FIG. 3, the dry-wet method generally generates higher quality ridge detail images in terms of areal minutiae covered. As the fingermarks were rubbed together prior to deposition, an even deposition of the endogenous compounds resulting in a uniform image of distribution was expected; the spray coat method appears to generate a much more discontinuous ridge pattern and a lot lower ion signal uniformity. The ion intensity was also generally higher when fingermarks were prepared using the dry wet method with the exception of the bad donor. However, even in this case, in terms of minutiae retrievable, relatively to the species imaged, the dry wet method is slightly better placed than the spray coat method. Overall these results are in agreement with previous work published by Aerni and collaborators [Aerni, H. R.; Cornett, D. S.; Caprioli, R. M.; *Anal. Chem.*, 2006, 78, 827-834]. In this work, the dusting technique was applied in a different way to the present work, as it was employed on biological tissues and was used as a seeding step to which matrix solution application followed either by spray coating or microspotting. However, in both cases, in agreement with the results shown here, a better homogeneity of matrix deposition over the tissue, as well as an increased ion signal intensity were demonstrated.

Ion species imaged in FIG. 3 were subjected to high resolution mass spectrometry profiling to ascertain their identity. The species at m/z 283.3, 311.3 and 668.6 were tentatively identified by High Mass Accuracy measurements as oleic acid, eicosenoic acid and amino-octadecanoic acid with mass accuracies of 1.1 ppm, 2.3 ppm and 1.1 ppm respectively.

Referring to FIG. 4, the reproducibility of the dry-wet method was also tested by imaging four fingermarks from the same donor. Average spectra were exported from Biomap to mMass, an open source multifunctional mass spectrometry software [Strohalm, M.; Kavan, D.; Novak, P.; Volny, M.; Havlicek, V. *Anal Chem*, 2010, 82, 4648-4651; Strohalm, M.; Hassman, M.; Košata, B.; Kodiček, M. *Rapid Commun Mass Spectrom*, 2008, 22, 905-908]. FIG. 4a reports the four mass spectra generated for the α-CHCA matrix peak at m/z 190. Spectra were not normalised. The ion peak signals are almost superimposable showing reproducibility in the application of the matrix. The lack of a perfect superimposition is likely due to the impossibility of obtaining four identical fingermark depositions as the pressure that the finger exerts on the surface will be inevitably slightly different. Before the deposition of ungroomed fingermarks, hands and fingers were wiped with alcohol wipes known to contain an antiseptic, dimethylbenzylammonium ion, which has previously been identified by these and other authors [Bradshaw, R.; Wolstenholme, R.; Clench, M. R.; Blackledge, R. D.; Ferguson L.; Francese, S. *Rapid Common Mass Spectrom*, 2011, 25, 415-422; Ferrer, I.; Furlong. E. *Environ Sci Technol*, 2001, 35, 2583] and observed to generate very good mass spectral images [Bradshaw, R.; Wolstenholme, R.; Clench, M. R.; Blackledge, R. D.; Ferguson L.; Francese, S. *Rapid Commun Mass Spectrom*, 2011, 25, 415-422]. Dimethylbenzylammonium ion mass spectra are therefore also reported as shown in FIG. 4b exhibiting a similar degree of ion intensity overlapping to that observed for the matrix. MALDI-MS images of this ion are also shown in FIG. 4c reflecting the average peak intensities observed in the mass spectra of the four replicates and the possibility to detect with constant clarity the 'delta' feature which is one of the minutiae exhibited by the particular fingermark examined.

Most importantly, the dry-wet method has a crucial feature which makes it altogether superior to the spray-coating method previously employed [Wolstenholme, R.; Bradshaw, R.; Clench, M. R.; Francese, S. *Rapid Commun Mass Spectrom*, 2009, 23, 3031]. This existing spray coating method in fact can only be applied to: i) fingermarks previously enhanced (provided that the enhancing method was compatible with the MALDI-MSI analysis) and ii) to fingermarks that were laid flat on an adequate MALDI support. Wolstenholme and collaborators used only one surface (aluminium sheets) for depositing and analysing the fingermark and, therefore, the technology could not be proven, at that time, to be helpful in real crime scene investigations. However, with the present dry-wet method that employs as enhancing powder an actual MALDI matrix, it is now possible to visually identity fingermarks on crime scene surfaces, lift and analyse them by MALDI-MSI.

A range of deposition surfaces have been tested to prove feasibility including non-porous surfaces such as metal, glass, plastic, and porous surfaces such as varnished wood and leather. The series of FIGS. 5A, 6A, 7A, 8A and 9A are photographs of fingermarks on different deposition surfaces prior to dusting with the matrix and the series of FIGS. 5B, 6B, 7B, 8B and 9B are the corresponding photographs post matrix dusting, with each surface comprising the same sample of deposited fingermark. The substrate surfaces tested included glass (FIG. 5 series), a metal (FIG. 6 series), wood (FIG. 7 series), plastic (FIG. 8 series) and leather (FIG. 9 series). In particular, images of an endogenous aminoacid (putative Lysine m/z 147), an endogenous fatty acid (oleic acid m/z 283) and an exogenous compound (dimethylbenzylammonium ion m/z 304) were obtained as shown in FIGS. 5 to 9, series C, D and E, respectively for each substrate. It is accepted that fingermarks on porous surfaces are more problematic to visualise than those on non-porous ones. As proving feasibility of the method is the objective, all the images are reported with differing contrast and brightness to enhance the ridge detail features in each case. This is how forensic investigators would treat the fingermark image for comparison as their goal is to obtain as many clear minutiae as possible. FIGS. 5A to 9E confirm that for all of the tested substrate surfaces it is possible to retrieve an image of endogenous and the selected exogenous compounds. In particular, the dimethylbenzylammonium ion exhibits the best image quality (grade 4), which, amongst other factors, could also be due to its relative amount compared to the two endogenous compounds selected. Although ranging in grade, putative lysine and oleic acid overall yield useful images, which could be superimposed using appropriate software to enhance the ridge pattern clarity.

In order to understand and improve the efficiency of the dry wet method, the matrix was considered in regards to its particles size. Four experiments were performed in which, upon dusting with different size matrix particles, the fingermarks of the good donor were submitted to SEM and to MALDI MSI to evaluate the impact of the matrix particle size on the quality of the ridge pattern in the MALDI MS image. In particular, prior to submission to SEM and MALDI MSI analyses, fingermark were: spray coated (experiment A), dusted with unground matrix used directly as the manufacturer sells it and solvent sprayed (experiment B), dusted with manually ground matrix and solvent sprayed (experiment C), dusted with mechanically ground and sieved matrix (<38 µm) followed by solvent spraying (experiment D), dusted with mechanically ground matrix (generating 10-20 µm particle size according to the manufacturer) followed by solvent spraying (experiment E). FIG. 10 shows the SEM micrographs of fingermarks spray coated and dusted with different particle size matrix and a MALDI MSI image of the fingermarks treated with the different matrix systems. As the matrix excess is blown off prior to solvent spraying, matrix co-crystal formation is mainly expected on the endogenous compound rich ridges of the fingermark. This is in fact observed and matrix co-crystals assemble on "lines" which are effectively the ridges. This is better viewed in FIG. 10 D1. For fingermarks treated with the dry-wet method, as a result of the different matrix powder pre-treatments, a decrease in the matrix co-crystals average length is observed along with a general increase in the density of distribution of the matrix co-crystals. In particular the matrix co-crystals average length is ~54 µm for experiment B (FIG. 10 B2), ~16 µm for experiment C (FIG. 10 C2), ~7 µm for experiment D (FIGS. 10 D2) and ~6 µm for experiment E (FIG. 10 E2). Correspondingly, the ridge pattern image quality of the dry-wet method treated fingermarks improves as the co-crystal average length decreases. It must be noted that, although the image resolution is dictated by the laser spot diameter so that matrix co-crystals with smaller diameter than that of the laser have no impact on it, the image coverage of a species evenly distributed on the given target, improves with decreasing the size of the co-crystals [Crossman, L.; McHugh, N. A.; Hsieh, Y; Korfmacher, W. A.; Chen, J. *Rapid Commun. Mass Spectrom.*, 2006, 20, 284]. In agreement with the above, the MALDI MSI images of the corresponding fingermarks show a dramatic increase of both the fingermark area coverage when considering the unground matrix dusted and the manually ground matrix dusted fingermarks (FIG. 10 B3 and FIG. 10 C3), and of the signal intensity when considering the manually ground matrix dusted and the mechanically ground and sieved dusted matrix fingermarks (FIGS. 10 C3 and D3). Dusting mechanically ground matrix (10-20 µm) on the fingermark generates very similar results to dusting mechanically ground and sieved matrix in terms of image coverage and intensity (FIGS. 10 D3 and E3). The spray coated fingermark presents mainly of amorphous species which would explain the generally lower signal intensity compared to the dry wet method as well as a poorer coverage of the ridge pattern. In these experiments the dry wet method is clearly superior to the spray coat one when the matrix was ground prior to dusting which is likely due to a higher number of crystals and better uniformity of crystallization. In the extreme case when the matrix was not ground, the quality of the image for the spray coated fingermark appears to be slightly better (grade 2) than that of the dry-wet method (grade 1) (FIG. 10 A3 and FIG. 10 B3). However, in relation to the image shown in FIG. 10 B3, it is important to bear in mind that the ability to produce multiple images for the same fingermark allows image overlay and thus provides enhanced coverage of the ridge pattern. Also, as benchtop ball mills are readily available enabling up to 20 g of matrix to be ground to <20 microns in less than 5 min, the use of unground matrix is conveniently avoidable. Finally, even with the bigger matrix particle size where the spray coat method may produce slightly better images than the dry wet method, because it is inapplicable in the field it is eliminated as a viable matrix deposition method for MALDI MS Imaging analyses.

The demonstrated applicability of the present dry-wet method to recover and analyse latent fingermarks by MALDI-MSI therefore complements the achievements of current forensic methodologies. The existing techniques suggested in the Home Office Scientific Development Branch (HOSDB) manual, are aimed solely at providing an image of the ridges on the fingertip, they are often not appropriate for a wide range of situations and they do not provide any additional information. Only in cases where a clear mark has been deposited will the existing techniques, if used correctly, allow a comparison. However, scene of crime marks are not ideal marks. They may be smudged, as a result of the articulation of the arm while the donor is holding an object, overlaid because of multiple contacts or any number of other actions resulting in ridges that are not sufficiently clear for comparison. In these cases it would be beneficial to have a protocol available, such as MALDI-MSI in combination with the present dry-wet deposition method that is configured to enable visualisation of the ridge pattern, but also provide chemical information which could potentially disclose donor dietary habits or drug use.

Accordingly, via the present method of sample preparation, MALDI-MSI is capable of detecting both endogenous and exogenous fingermark chemical components in one analysis and simultaneously to providing an image of the fingermark ridge pattern. By preparing the sample appropriately, it is demonstrated that MALDI-MSI can be used for fingermarks deposited on a range of surfaces and in such a way, that recovery from the scene could be integrated easily with current crime scene investigator practice for subsequent instrumental analysis, importantly, remote from the crime scene. The novel two step matrix deposition method that has been developed allows evidence to be photographed and exposed to both UV light and fluorescent radiation enabling even clearer images to be obtained. This possibility allows the kind of legal evidence to be generated prior to subsequent MALDI-MSI analysis which, by providing chemical information, potentially adds intelligence to the case under investigation.

The invention claimed is:

1. A method of preparing a matrix assisted laser desorption ionization mass spectrometry imaging (MALDI-MSI) fingermark sample comprising:
providing a fingermark;
dusting the fingermark with a dry MALDI-MSI matrix powder;
removing excess matrix powder from the fingermark; and
co-crystallizing the matrix powder with analytes from the fingermark by spraying the dusted fingermark with a solvent in which both the matrix powder and the dusted fingermark are soluble,
wherein co-crystallizing the matrix powder with the analytes minimizes analyte delocalization to preserve ridge details and minutiae in a chemical image of the fingermark sample, and
wherein the chemical image is obtained by MALDI-MSI.

2. The method as claimed in claim 1 further comprising lifting the fingermark sample from a surface upon which the fingermark sample is deposited using an adhesive backed strip, pad or tape.

3. The method as claimed in claim 2 wherein the strip, pad or tape is crime scene investigation (CSI) tape.

4. The method as claimed in claim 3 wherein the step of spraying the dusted fingermark sample comprises spraying the fingermark sample adhered to the strip, pad or tape with the solvent.

5. The method as claimed in claim 4 further comprising introducing the lifted fingermark sample on the strip, pad or tape into a MALDI mass spectrometer with imaging capabilities.

6. The method as claimed in claim 5 further comprising obtaining at least one chemical image of the fingermark sample by MALDI-MSI.

7. The method as claimed in claim 1 wherein a particle size of the matrix powder is in the range of 5 μm to 120 μm.

8. The method as claimed in claim 7 wherein a particle size of the matrix powder is in the range of 10 μm to 30 μm.

9. The method as claimed in claim 1 wherein the matrix is configured as one or more of an absorber of UV radiation and a fluorescent compound.

10. The method as claimed in claim 1 wherein the step of spraying the dusted fingermark sample comprises spraying the solvent onto the dusted fingermark sample as a fine mist.

11. The method as claimed in claim 10 comprising three successive spray applications of the fine mist onto the fingermark sample.

12. The method as claimed in claim 11 comprising creating the fine mist using an automatic pneumatic sprayer device.

13. A method of matrix assisted laser desorption ionization mass spectrometry imaging (MALDI-MSI) comprising:
preparing a fingermark sample according to claim 1;
introducing the sample into a MALDI imaging mass spectrometer;
delivering a laser beam to the fingermark sample within the mass spectrometer; and
generating a chemical image of the fingermark sample.

14. A method of creating a plurality of images of a fingermark comprising:
preparing a fingermark sample according to claim 1;
introducing the prepared fingermark sample into a MALDI imaging mass spectrometer;
obtaining at least one chemical image of the fingermark sample using a MALDI mass spectrometer with imaging capabilities,
wherein the ridge details and minutiae in the chemical image are preserved.

15. The method as claimed in claim 14 further comprising obtaining a fluorescent image of the prepared fingermark sample using a fluorescent microscope.

16. The method as claimed in claim 14 further comprising obtaining a UV image of the prepared fingermark sample using a UV light source and a still and/or video camera.

17. The method as claimed in claim 14, wherein the solvent comprises 70:30 ACN/0.5% TFA.

18. The method as claimed in claim 14, wherein the ridge detail and minutiae are classified as grade 4 (full development) under the HOSDB grading system.

19. The method as claimed in claim 14, further comprising lifting the fingermark sample from a porous surface.

20. The method as claimed in claim 14, wherein the chemical image comprises an imaging pattern derived from distribution of one or more of endogenous amino acids, endogenous fatty acids, endogenous diacylglycerols, and endogenous triacylglycerols within the fingermark sample.

* * * * *